US006582929B2

(12) United States Patent
Dunfee et al.

(10) Patent No.: US 6,582,929 B2
(45) Date of Patent: Jun. 24, 2003

(54) METHOD FOR MINIMIZING OPTICAL INTERFERENCE DURING ANTIBIOTIC SUSCEPTIBILITY READINGS IN A MICROBIOLOGICAL ANALYZER

(75) Inventors: William David Dunfee, New Castle, DE (US); Bruce McLean Gemmell, Wilmington, DE (US); Edward Stephen Kaminski, Elkton, MD (US); John Charles Mazza, Newark, DE (US); Edward Francis Farina, Oxford, PA (US); Frank Stephen Krufka, Kirkwood, PA (US)

(73) Assignee: Dade Microscan Inc., West Sacramento, CA (US)

( * ) Notice: Subject to any disclaimer, the term of this patent is extended or adjusted under 35 U.S.C. 154(b) by 84 days.

(21) Appl. No.: 09/841,392

(22) Filed: Apr. 24, 2001

(65) Prior Publication Data

US 2002/0155516 A1 Oct. 24, 2002

(51) Int. Cl.⁷ .................................................. C12Q 1/18
(52) U.S. Cl. ...................................... 435/32; 435/288.4
(58) Field of Search ................................ 435/32, 287.1, 435/288.4, 288.5; 422/58, 63, 67; 436/43, 47, 165

(56) References Cited

U.S. PATENT DOCUMENTS

| 4,448,534 A | * | 5/1984 | Wertz et al. ................. 356/435 |
| 4,856,073 A | | 8/1989 | Farber et al. .................... 382/6 |
| 5,746,980 A | * | 5/1998 | O'Bear et al. ............... 422/102 |
| 5,762,873 A | | 6/1998 | Fanning et al. ................ 422/65 |
| 5,856,193 A | | 1/1999 | Fanning et al. ................ 436/48 |
| 5,888,455 A | | 3/1999 | Seaton ......................... 422/65 |
| 5,922,593 A | | 7/1999 | Livingston ............... 435/288.5 |
| 5,925,884 A | | 7/1999 | Robinson ................. 250/458.1 |
| 5,932,177 A | | 8/1999 | O'Bear et al. ............... 422/102 |
| 6,096,272 A | * | 8/2000 | Clark et al. .................... 422/64 |

\* cited by examiner

*Primary Examiner*—Ralph Gitomer
(74) *Attorney, Agent, or Firm*—Leland K. Jordan

(57) ABSTRACT

Performing antibiotic testing on samples contained in test arrays by orienting the arrays relative to the direction of gravity so that test solution within the microwells is drawn downwards and air within the microwells is forced to the uppermost portion of the test array. Antibiotic testing is conducted using an interrogating beam of radiation passing horizontally through the microwells at locations devoid of air bubbles.

8 Claims, 12 Drawing Sheets

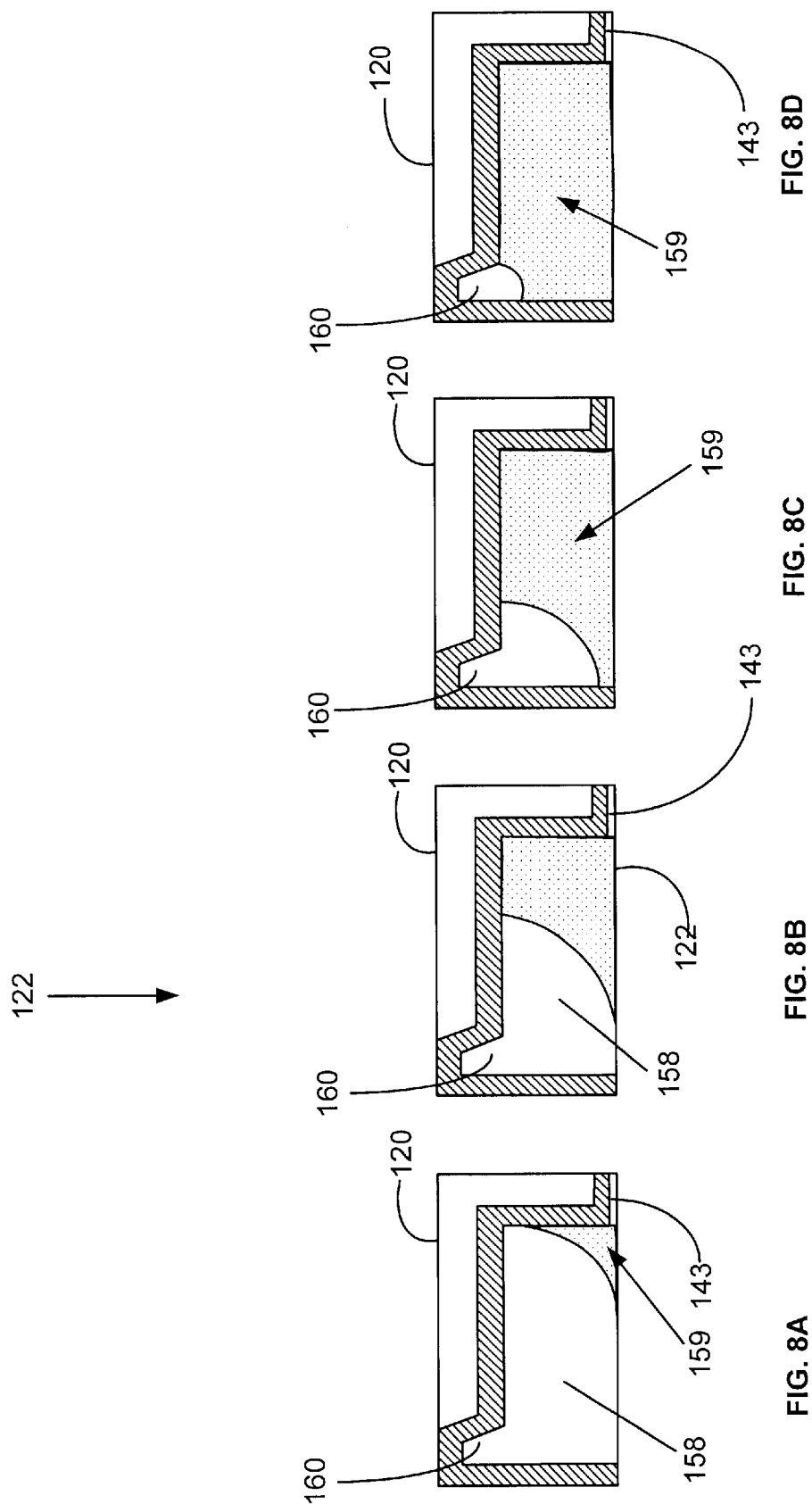

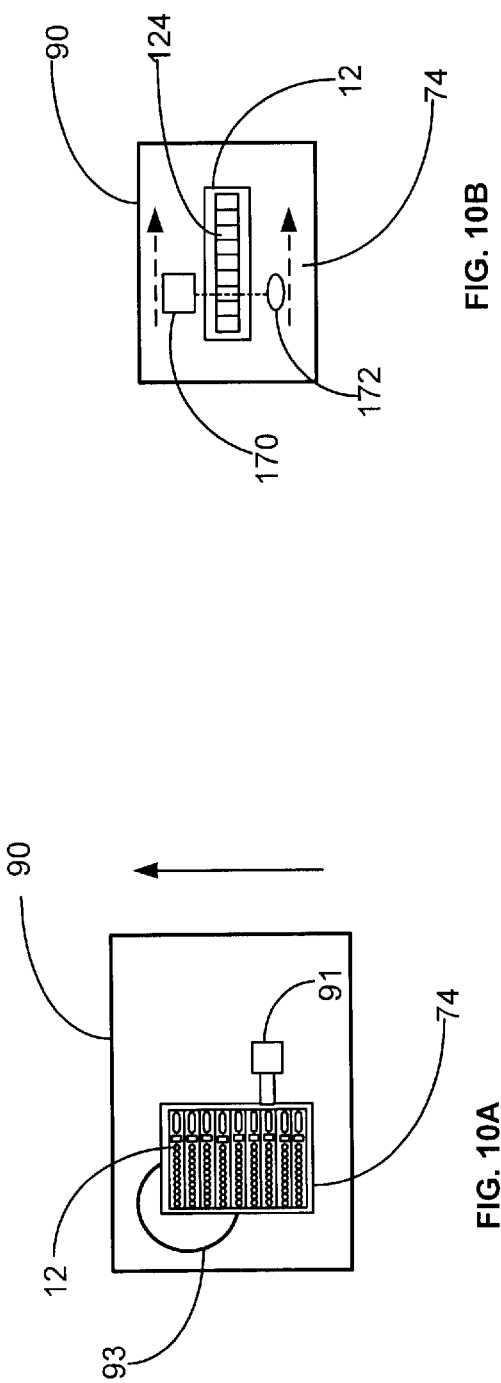
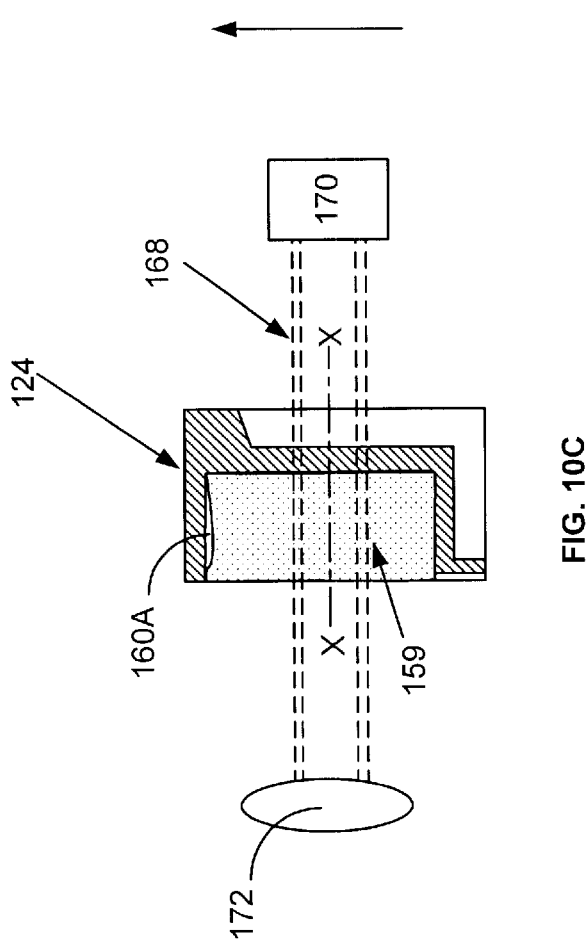
FIG. 10B
FIG. 10C
FIG. 10A

METHOD FOR MINIMIZING OPTICAL INTERFERENCE DURING ANTIBIOTIC SUSCEPTIBILITY READINGS IN A MICROBIOLOGICAL ANALYZER

FIELD OF THE INVENTION

The present invention relates to microbiological test arrays suitable for use in automated analyzers employing a carrier to transport such arrays between various functional stations. More particularly, the present invention provides means to eliminate unwanted air bubbles from interfering with optical measurements performed on liquids contained in microwells within the array.

BACKGROUND OF THE INVENTION

Various types of tests related to patient diagnosis and therapy can be performed by analysis of a biological sample. Biological samples containing the patient's microorganisms are taken from a patient's infections, bodily fluids or abscesses and are typically placed in test panels or arrays, combined with various reagents, incubated, and analyzed to aid in treatment of the patient. Automated biochemical analyzers have been developed to meet the needs of health care facilities and other institutions to facilitate analysis of patient samples and to improve the accuracy and reliability of assay results when compared to analysis using manual operations. However, with ever changing bacterial genera and newly discovered antibiotics, the demand for biochemical testing has increased in both complexity and in volume. Because of these greater demands in conjunction with the expense and scarcity of floor space within health care institutions and the pressure to provide clinical results at lower costs, it has become important to simultaneously perform various types of biochemical tests within a highly automated and compact analyzer that operates with minimal clinician attention using cost-effective techniques.

An important family of automated microbiological analyzers function as a diagnostic tool for determining an antibiotic effective in controlling growth of the microorganism. In performing these test, in vitroantimicrobic susceptibility patterns of microorganisms isolated from biological samples are ascertained. Such analyzers have historically placed selected biochemicals into a plurality of small sample test wells in panels or arrays that contain different antimicrobics against known microorganisms in serial dilutions. Minimum Inhibitory Concentrations (MIC) of antibiotics effective against the microorganism are determined by color changes, fluorescence changes, or the degree of cloudiness (turbidity) in the sample test wells created in the arrays. By examining the signal patterns generated, MIC analyses are performed by computer controlled microbiological analyzers to provide advantages in reproducibility, reduction in processing time, avoidance of transcription errors and standardization for all tests run in the laboratory.

The use of microbiological test trays and the techniques employed in MIC tests, also known as Antibiotic Susceptibility Testing, AST, of microorganisms are also well known. AST tests are essentially broth dilution susceptibility tests using wells filled with inoculum and a growth broth, called herein a inoculum-broth solution, and increasing concentrations of a number of different antibiotics, or antimicrobial agents. The different antimicrobial agents are typically diluted in Mueller-Hinton broth with calcium and magnesium in chromogenic panels or diluted in autoclaved water with a fluorogenic compound in fluorogenic panels. The antimicrobials are diluted to concentrations that include those of clinical interest. After incubation, the turbidity or fluorescence, generally measured using a beam of radiation passing through the solution, will be less or non-existent in wells where growth has been inhibited by the antimicrobics in those wells. The analyzer compares each test well reading with a threshold value. The threshold value is a fixed number corresponding to a certain percentage of relative absorbency or fluorescence which corresponds to clinically significant growth. The MIC of each antimicrobial agent is measured either directly as visible growth, or indirectly as an increase in fluorescence.

Important challenges that must be taken into consideration when designing cost-effective, automated biochemical analyzers include the volume of reagents required per test and the cost of the disposable test panel or array. Because they are small and may be produced using mass-production, plastic injection molding techniques, it is cost-advantageous to use small sized test devices having a number of very microwells for performing AST tests. Such small sized test devices are readily amenable to automatic handling and may be used once and disposed with minimize expense. AST test devices typically consist of a plurality of adjacent microwells aligned in some sort of an array, each microwell functioning as a reaction vessel for the above mentioned biochemical reactions involving a solid phase media and a liquid phase containing a sample to be tested. An aliquot of the sample is placed in each microwell along with appropriate antibiotic reagents. AST testing usually requires that the test trays be incubated at a controlled temperature for a period of time so that an observable reaction between the sample and reagent occurs; at predetermined time intervals, each microwell of the test tray is examined for an indication of changes in color change, turbidity, or the like.

Filling the number of microwells with the required inoculum and/or reagents presents several technical challenges that are made increasingly difficult as the size of the microwells is reduced. These challenges include providing a uniformity of fill, maintaining the integrity of solution in a microwell, minimizing the effects of air bubbles that impede test observations, etc. Efforts have been made to address these challenges along with other problems and these generally employ a vacuum technique in filling microwells within a test array via an interconnected number of micro-sized channels including the introduction of especially formed features to trap air bubbles away from solution to be optically tested.

U.S. Pat. No. 5,932,177 provides a test sample card as typically used in biochemical analysis, having a number of same-sized rectangular shaped sample wells and fluid flow by means of a plurality of through-channels which route the fluid flow of samples along both the front and back surfaces of the card. Elevated bubble traps are provided, as are integral interrupt slots for sensing card position and alignment.

U.S. Pat. No. 5,922,593 discloses a microbiological test panel having a plurality of translucent cups extending from a first side of a planar surface, and a chassis having a plurality of open-ended tubes formed in the chassis. The chassis includes a plurality of raised passage walls on a second side of the planar surface that form passageways over the openings at the bottom ends of the tubes. One end of the passageway has an opening to allow an inoculum to flow through the passageway. The chassis further comprises an air communication port formed as an open-ended tube extending from the second side of the planar surface.

U.S. Pat. No. 5,746,980 discloses a test sample card with a fluid intake port and sample wells disposed between its opposite surfaces. A fluid channel network connects the fluid intake port to the sample wells and a bubble trap is connected to at least one of the sample wells by a conduit with formed in said first surface of the card. The bubble trap is formed as a depression extending part way through the card body and is covered by sealant tape.

From this discussion, it may be seen that there remains a need for an optical testing technique that simply and inexpensively solves the challenges associated with generation of air bubbles in micro-sized test arrays used in a microbiological analyzer. In particular, there is a need for a simple and inexpensive method for minimizing optical interference caused by unwanted air within the optical reading path during antibiotic susceptibility readings in a microbiological analyzer.

SUMMARY OF THE INVENTION

The present invention meets the foregoing needs by providing a method for testing a microbiological test array having a plurality of microwells prefilled with known amounts of different antibiotics in which unwanted air is removed from the region of optical testing without resorting to use of bubble traps. The microbiological test array have a generally flat lower surface with a plurality of upwardly projecting microwells connected by a number of microchannels to an open reservoir formed in a upper surface of the test array. The reservoir has an opening to permit a liquid inoculum-broth solution to flow into each of the microwells during a vacuum filling process. During AST testing, the test array is generally "horizontally oriented" relative to the direction of gravity forces so that test solution within the microwells is drawn downwards and air within the microwells is forced to the uppermost portion of the test array. In this horizontal position, AST readings are conducted using an interrogating beam of radiation passing horizontally through the microwells at locations devoid of air bubbles. To achieve the generally horizontal position, the test array is typically moved so that the axis of the originally upwardly projecting microwells is rotated about ninety degrees relative to its initial alignment.

BRIEF DESCRIPTION OF THE DRAWINGS

These and other features and advantages of the present invention can best be understood by reference to the detailed description of the preferred embodiments set forth below taken with the drawings in which:

FIG. 8 is illustrative of a liquid sample filling process using the AST test array of FIG. 3;

DETAILED DESCRIPTION OF THE PREFERRED EMBODIMENTS

Figure 1:
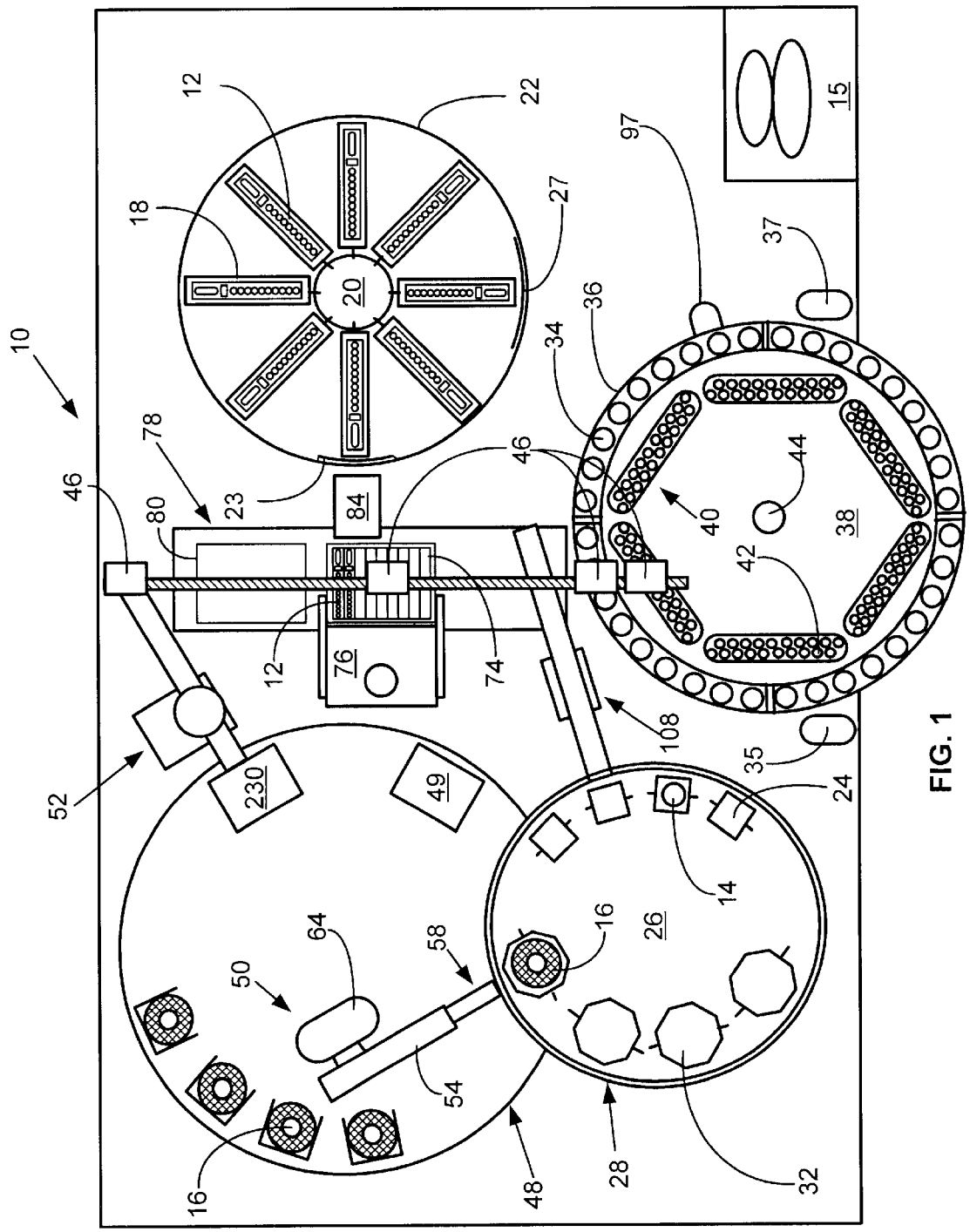
FIG. 1 is a simplified schematic plan view of an automated microbiological analyzer illustrative of the present invention.
Figure 2:
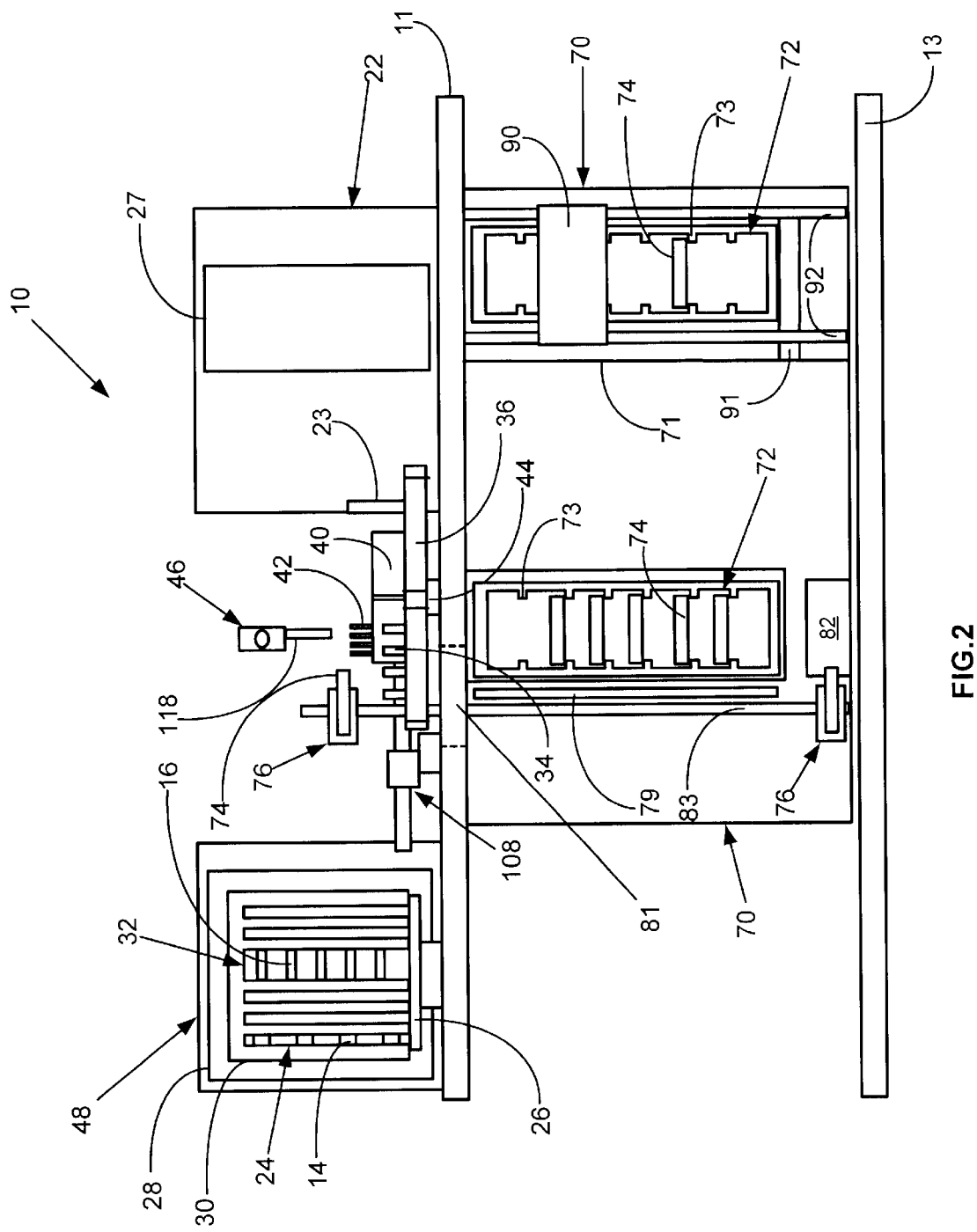
FIG. 2 is a simplified schematic elevation view of the automated microbiological analyzer of FIG. 1.

FIG. 1 schematically illustrates an embodiment of the automated random access microbiological analyzer 10 of the present invention, the analyzer 10 having an on-board inventory of AST test arrays 12 adapted for performing different AST tests, a plurality of broth containers 14 (also seen in FIG. 2) adapted to provide different growth media as may be required for AST testing, and a plurality of ID test rotors 16 adapted for performing different ID tests. The inventory of different AST test arrays 12 are maintained within analyzer 10 in different rectangularity elongate AST test array canisters 18. The AST canisters 18 are attached to a rotatable post 20, hereinafter called the AST canister post 20; the AST canister post 20, AST canisters 18 and AST test arrays 12 are housed within an environmentally controlled AST inventory chamber 22 (top portion is removed for purposes of illustration in FIG. 1). The different AST test arrays 12 are preloaded with increasing concentrations of a number of different antibiotics, or antimicrobial agents, as required to perform AST testing on a patient sample, also called inoculum herein, as requested by a physician. In FIG. 2, the AST inventory chamber 22 is shown with a first door 23 or seal 23 provided to allow operating access to any one of the AST canisters 18 when AST canisters 18 are rotated by AST canister post 20 into alignment with an AST array dispenser 84 described later. The AST inventory chamber 22 also has a second door 27 to allow the AST canisters 18 to be mounted onto AST canister post 20 by an operator.

The plurality of different broth cups or containers 14 (FIG. 2, left side) are maintained in an on-board inventory within analyzer 10 in different tube-like broth canisters 24, and the broth canisters 24 are maintained on a rotatable carousel 26, hereinafter called the B/ID carousel 26, adapted to rotate the B/ID carousel 26 to present a required broth canister 24 and broth container 14 to a broth container handling device 108. The B/ID carousel 26 is housed within an environmentally controlled B/ID chamber 28 (shown with its top portion removed for purposes of illustration). The different broth containers 14 are preloaded with a number of different standard broth solutions that act as a growth media during AST testing. In FIG. 2, the B/ID chamber 28 is shown with a door 30 in an opened position to allow operating access to the inside of the B/ID chamber 28. The broth canisters 24 are shown as being made of a transparent material or as cut-away in order to shown four broth containers 14 contained within the broth canisters 24.

In a similar manner, the analyzer 10 has an on-board inventory of different ID test rotors 16 that are maintained in an inventory within analyzer 10 in different tube-like ID canisters 32 and the ID canisters 32 are maintained along with broth canisters 24 on the B/ID carousel 26 within B/ID chamber 28. The different ID test rotors 16 are preloaded with substrates and reagents that are selected to produce a known pattern of measurable reaction signals which correspond to various known microorganisms.

Patient samples are presented to the analyzer 10 in open sample tubes 34 placed in openings in a number of sample tube holders 36 located near the periphery of a rotatable circular tray, known hereinafter as S/PT tray 38, rotatable by a S/PT tray motor 44. Sample tube holders 36 are generally curved, each forming a sector of the circumference of a circle. Four of such sample tube holders 36 are seen in FIG. 1 supported on rotatable tray 38, however any number of sample tube holders 36 may be sized and adapted to fit onto the circular tray 38. Conventional bar-code readers 35 are placed proximate sample tube holders 36 so as to determine the identity of sample tubes 34 and a turbidity reader 37 is similarly placed so as to confirm that the concentration of microbiological organisms within sample tubes 34 is within a predetermined range of acceptable values. A sample dilution station 97 is also located proximate S/PT tray 38 and is adapted to dilute sample contained in sample tubes 34 if the concentration of microorganisms in sample liquid carried within tubes 34 is determined by turbidity reader 37 to be higher than an allowable range.

The S/PT tray 38 also supports a number of pipette tip holders 40 located in the innermost portion of S/PT tray 38. Pipette tip holders 40 are generally elongate and may have a curved shape and each pipette tip holder 40 is adapted to hold a plurality of disposable pipette tips 42. Six of such pipette tip holders 40 are seen in FIG. 1, however any number of pipette tip holders 40 may be sized and adapted to fit onto the S/PT tray 38. The S/PT tray 38 may be rotated by motor 44 so as to present any of the pipette tips 42 and any of the open sample tubes 34 to a pipetting apparatus 46. The pipetting apparatus 46 is adapted to remove one of the pipette tips 42 from pipette tip holder 40, to insert the pipette tip 42 into an open sample tube 34, and to aspirate a known amount of patient sample from the sample tube 34 into the pipette tip 42. The pipetting apparatus 46 is further adapted to dispense a known amount of patient sample from pipette tip 42 into a broth container 14.

S/PT tray 38, pipetting apparatus 46, B/ID chamber 28, AST inventory chamber 22, and ID incubation and testing chamber 48 are supported above an upper operating plate 11 that provides a first operating plane for analyzer 10. A lower base plate 13, typically mounted on rollers, provides a second operating plane for additional structure for analyzer 10.

Analyzer 10 comprises two separate incubation and analysis chambers as required for ID and AST testing. An ID incubation and analysis chamber 48 is seen in the top plan schematic view of FIG. 1 with its uppermost surface removed to expose an interior portion in which an ID robotic device 50 is adapted to remove different ID test rotors 16 from ID canisters 32 and to then move the ID test rotors 16 to and from an ID rotor filling and centrifuging apparatus 52 moveable between the ID incubation chamber 48 and a sample pipetting and delivery system 60 described hereinafter. Devices that perform the functions of robotic device 50 are well known in the art as computer-controlled pick-and-place robotic devices.

In FIG. 2, an AST incubation and analysis chamber 70 is seen located below the operating plate 11 with a first side surface portion 71 opened to reveal an interior section in which a number of rotatable AST incubation racks 72 support a number of AST carriers 74, FIG. 7, the AST carriers 74 being adapted as described hereinafter to hold a number of AST test arrays 12 as they are transported throughout analyzer 10. An AST carrier transporter 76 is mounted on a vertically oriented AST transport rod 83 and is adapted to be movable from above the upper operating plate 11 to above the lower base plate 13. The AST carrier transporter 76 is shown in uppermost and lowermost positions in FIG. 2 for purposes of explanation even though there is only one such AST carrier transporter 76. In the uppermost position above the operating plate 11, as best seen in FIG. 1, the AST carrier transporter 76 can access an AST array carrier 74 transported on an AST carrier transport 78 and lower the AST array carrier 74 through an AST transport opening 81 in the operating plate 11. In the lowermost position, AST carrier transporter 76 is adapted to deposit an AST array carrier 74 into an AST vacuum filling station 82 positioned on the lower base plate 13 described hereinafter.

Figure 3:
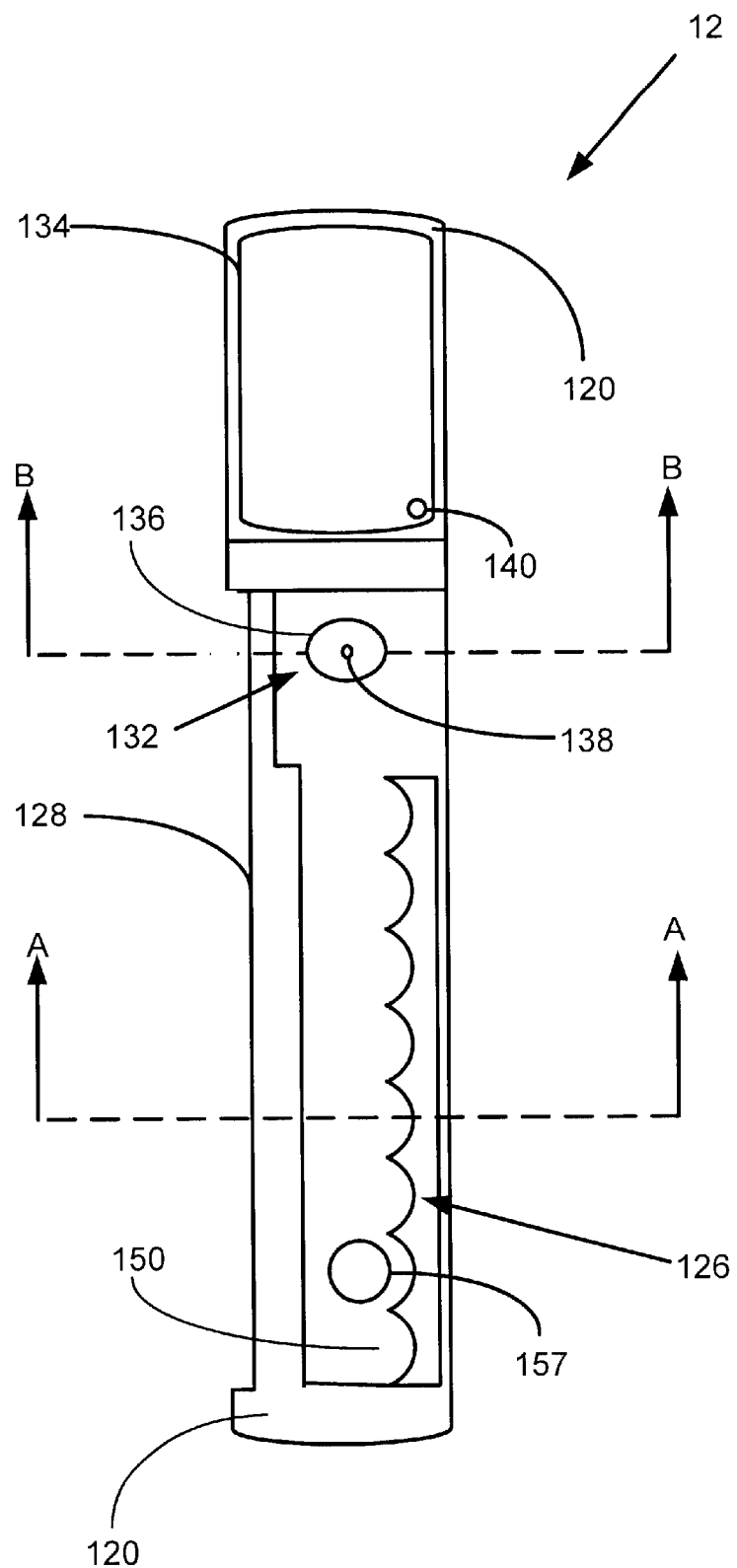
FIG. 3 is a top view of an AST test array useful within the analyzer of FIG. 1.
Figure 4A:
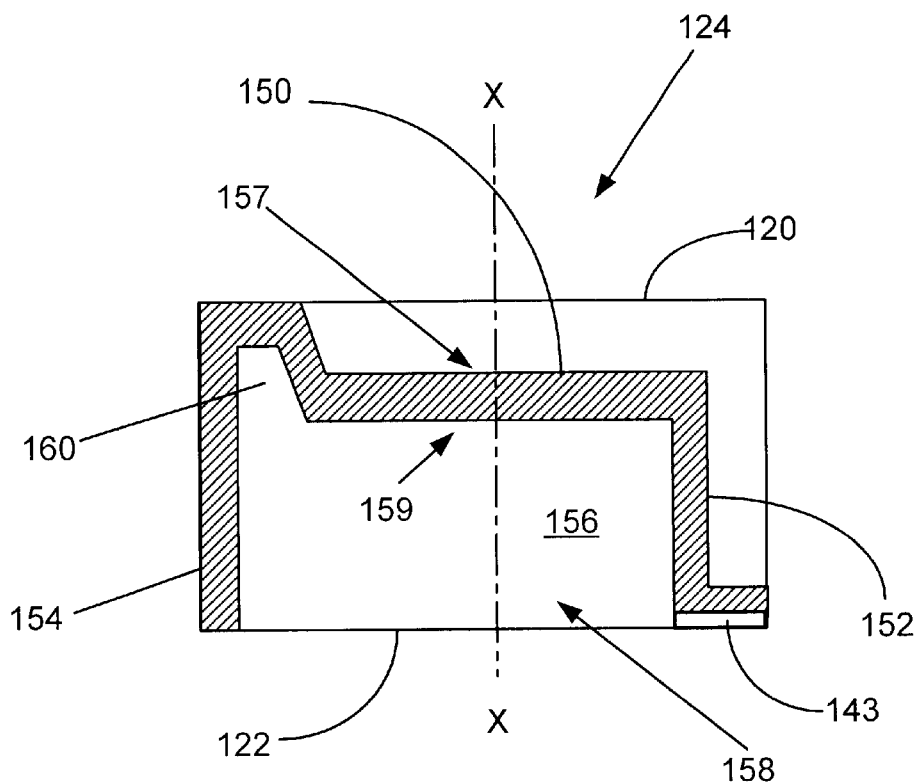
FIGS. 4A and 4B are cross-section views of the AST test array of FIG. 3.
Figure 4B:
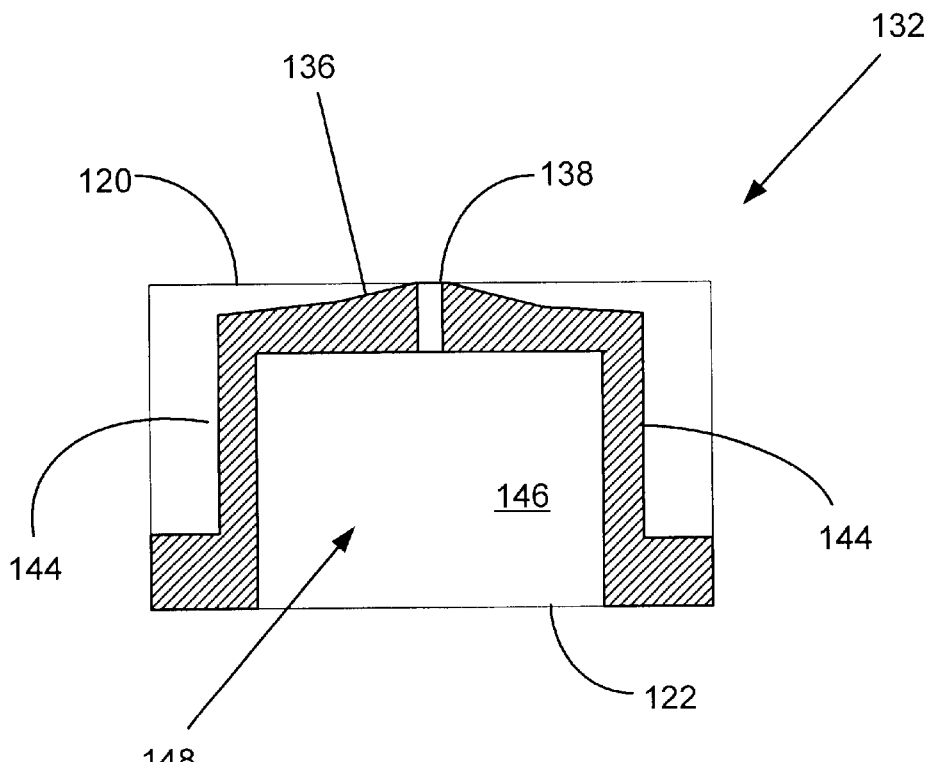
Figure 5:
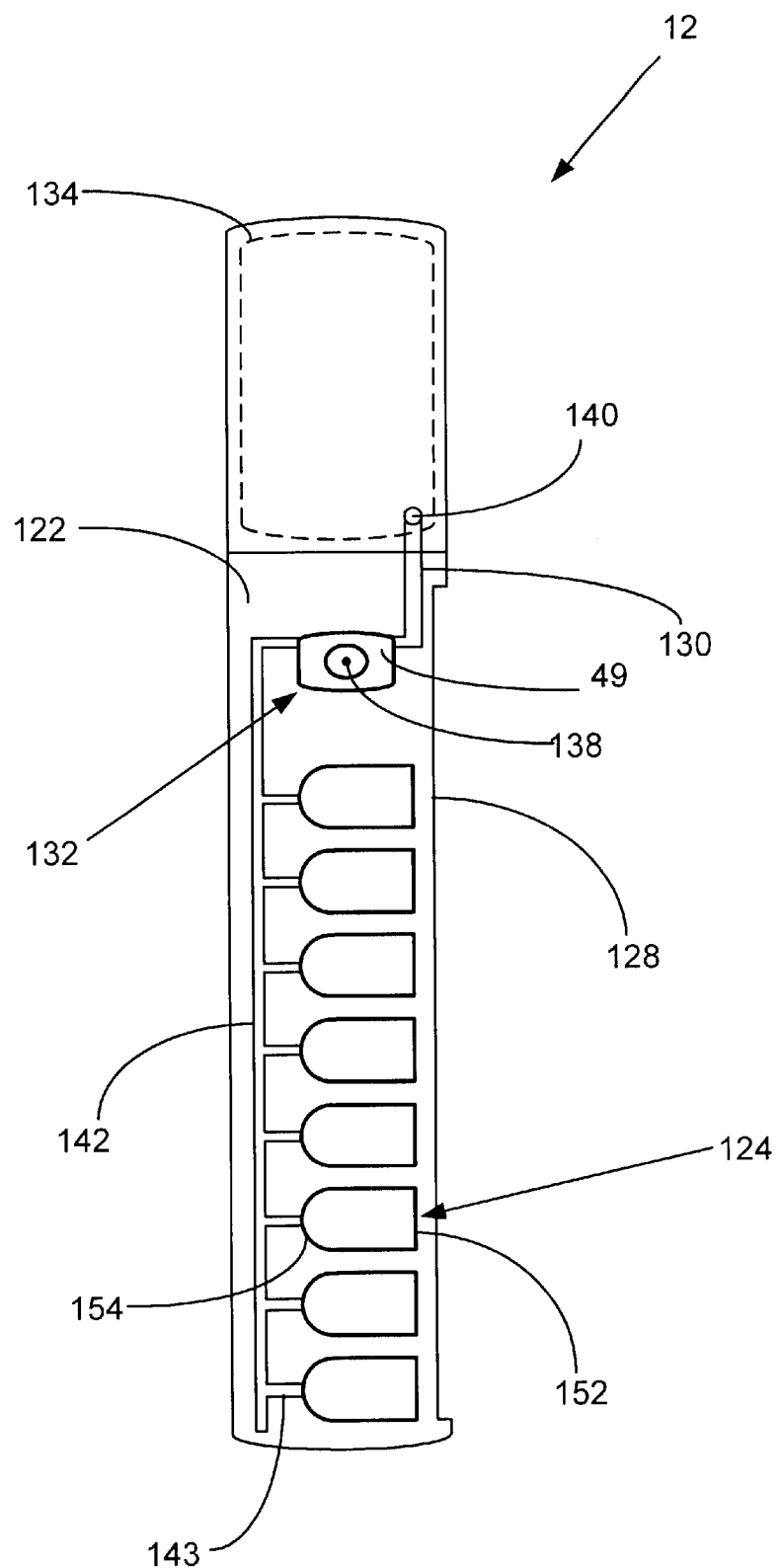
FIG. 5 is a bottom view of the AST test array of FIG. 3.

FIG. 3 shows the upper top surface 120 of an AST array 12 as containing relatively structured features described hereinafter and FIG. 5 shows the lower bottom surface 122 of an AST array 12 as being relatively flat. As described in a co-pending U. S. patent application Ser. No.: 09/795,823 each AST array 12 has an elongate length and a plurality of upwardly projecting AST microwells 124 formed in the bottom surface 120 as a linear row of single microwells 124 parallel to the length of the array 12. Top surface 120 and bottom surface 122 are on opposing surfaces and are separated by an indented sidewall 126 and an opposed sidewall 128. A sacrificial evaporation well 132 is formed in the bottom surface 122 of the test array upwardly projecting from an open portion of the bottom surface 122 and disposed between the row of microwells 124 and a reservoir 134. Evaporation well 132 is connected by a first microchannel 130 to the reservoir 134. Evaporation well 132 has a closed dome-shaped upper well surface 136 proximate the top surface 120 of the test array with a sealable vacuum port 138 formed therein as an opening in the dome-shaped upper well surface 136 of the evaporation well 132, as seen in FIG. 4B depicting a cross-section view along B—B of FIG. 3. Microwells 124 have the general shape of a closed well projecting upwards from the bottom surface 122 of the array 12 with a depth of about three-fourths the thickness of array 12, as seen in FIG. 4A depicting a cross-section view along lines A—A of FIG. 3, and have their openings along the bottom surface 122 of array 12. FIG. 4A shows each microwell 124 having a central axis X—X projecting upwardly from the base 122 of the array 12 through the central top surface 150 of each microwell 124. During the time AST test arrays 12 are transported throughout analyzer 10, the central axis X—X of each microwell 124 is generally vertically oriented along the direction of gravitational pull. As described hereinafter in conjunction with FIG. 10, the central axis X—X of each microwell 124 of FIG. 5A may be horizontally oriented during AST testing.

FIG. 4A illustrates the microwells 124 as having a top surface 150 portion of array 12, a rounded endwall portion 152 of the indented sidewall 126, a flat endwall 154 of the indented sidewall 126 and two parallel sidewalls 156. Both endwalls 152 and 154 are formed substantially perpendicular to the lower bottom surface 122 of array 12 and are separated by the two parallel sidewalls 156. The irregular top surface 150, the flat endwall portion 154, and the rounded endwall portion 152 cooperate to define a small AST reaction chamber 158. In one embodiment, the top surface 150 is shaped to form a recessed top edge portion 160 of AST reaction chamber 158 that functions as a bubble trap 160 for bubbles that may be generated when inoculum-broth solution is dispensed from reservoir 134 to sacrificial well 132 and test microwells 124. It has been discovered that when the microwells 124 are shaped as described herein, and when connecting microchannel 143 is positioned on the opposite surface of microwell 124 across from the bubble trap 160, bubble trap 160 is effective in capturing bubbles when microwell 124 is comprised of a generally hydrophilic material, like styrene. It has been observed that with such an arrangement, as inoculum-broth solution flows into microwell 124, air remaining within microwell 124 is urged by the expanding inoculum-broth solution without leaving any entrapped air pockets in the critical upper central area of the AST reaction chamber 158. Such a filling is pictorially illustrated in FIGS. 8A–D.

In an exemplary embodiment, the upper top surface 120 and lower bottom surface 122 are about 0.3–0.4 inches wide, the indented sidewall 126 is about 0.2–0.25 inches in height and the elongate dimension of the test array 12 is about 2.5–3.0 inches in length. In such an embodiment, the microchannel 42 would be sized with a width and depth of about 0.010 to 0.020 inches. Preferably, the AST test array 12 is constructed of a moldable plastic material like styrene, but other types of material can be used. Most preferably, the material used in constructing array 12 is generally translucent, so as to allow uninterrupted transmission of light through microwells 124 during AST testing in the microbiological analyzer 10.

In one embodiment, and using the process described later in conjunction with FIG. 9A–9G, AST testing may be accomplished by directing a beam of interrogating radiation from above or below each AST array 12 through a upper central arc portion 157 of the top surface 150 of each microwell 124 and measuring the degree of absorption or change in color or generation of a fluorescent signal using a calorimetric or fluorometric photodetector located below or above each microwell 124. Axis X—X of the AST test array 12 of FIG. 5 is generally vertically oriented during such AST testing. For this reason, the upper center portion 157 of the top surface 150 of every microwell 124 and the lower center portion 159 of the top surface 150 of every microwell 124, both intersected by microwell axis X—X, are molded so as to have a surface finish smoothness equivalent to or more smooth than SPI #A-1 grade #3 diamond buff in order to minimize optical interference.

The sacrificial evaporation well 132, best seen in FIG. 4B, is designed to provide an evaporation chamber 148 from which sacrificial evaporation of inoculum-broth solutions may take place, thereby inhibiting evaporation of solution from microwells 124. Evaporation from microwells 124 is inhibited because evaporation initially must occur from within short microchannel 130 and then from the sacrificial evaporation chamber 148 before evaporation might occur from long microchannel 142 and microwells 124. Evaporation chamber 148 further provides the sealable vacuum port 138 through which air contained within microwells 124 may be evacuated so that air within microwells 124 does not bubble through broth in the reservoir 134 during evacuation and generate air bubbles within inoculum-broth solutions. After evacuation, vacuum port 138 is subsequently sealed so as to generate a flow of inoculum-broth solution from reservoir 134 into the microwells 124.

As seen in FIG. 5, first microchannel 130 is formed as a open groove in the bottom surface 122 of the array 12 and connects the evaporation well 132 to a open top rectangular shaped inoculum-broth solution receiving reservoir 134 best seen in FIG. 3, the reservoir 134 having a closed bottom illustrated by dashed lines in FIG. 5. One end of the bottom of the reservoir 134 has a flow opening 140 also illustrated in FIG. 5 to allow inoculum-broth solution dispensed into the open top of reservoir 134 to flow from reservoir 134 through first microchannel 130, firstly into the sacrificial evaporation well 132 and therefrom to a second microchannel 142 and therefrom sequentially through a number of connecting microchannels 143 to each of the series of microwells 124. The open surface portions of first and second microchannels 130 and 142, connecting microchannel 143, flow opening 140, sacrificial evaporation well 132, and microwells 124 along the bottom surface 120 of array 12 are closed by sealing over with a layer of adhesive film during a manufacturing process in which antimicrobics of clinical interest are placed in the different microwells 124 but not in the sacrificial evaporation well 132. Optionally, one microwell 124 may be left empty of antimicrobics for use in generating a reference signal during optical analysis.

An AST array dispenser 84 is seen in FIG. 1 as being disposed between the AST chamber 22 and AST array carrier 74. The AST array dispenser 84 is adapted to remove a AST test arrays 12 from AST canisters 18 in the form of a singulated stream and to successively place the AST array 12 within empty AST array slots 86 formed within an AST array carrier 74 (FIG. 7). AST arrays 12 are loaded into the AST array carrier 74 in an initial vertical orientation in which the central axis X—X (seen in FIG. 4A) of each microwell is vertically oriented. As described later in conjunction with FIGS. 2A and 10A–C, during AST incubation and testing, the AST array carrier 74 is re-positioned into a generally horizontal orientation in which the central axis X—X of each microwell is rotated about ninety degrees from its initial vertical orientation so as to cause air bubbles lying within the path of a beam of interrogating radiation to move upwards and out of that optical reading path. AST array dispenser 84 comprises an ejection means operable with an alignment means and a biasing means to precisely align and eject the lowermost AST test array 12 from any one of the AST canisters 18 into an empty parallel slot 86 when slot 86 is aligned by AST carrier transport 78 with the elongate dimension of a first AST test array 12 having therein the antibiotics as required to perform a first AST test ordered by a physician. Subsequent to loading of the first AST test array 12 into the first parallel slot 86, the AST carrier transport indexes the AST array carrier 74 step-wise relative to the AST array dispenser 84 so as to align a second empty parallel slot 86 in AST array carrier 74. Simultaneously with the AST array carrier 74 being moved relative to the AST array dispenser 84, the AST canister post 20 is rotated to present to AST array dispenser 84 another of the AST canisters 18 housing the particular AST test arrays 12 preloaded with the appropriate antibiotics required to perform another AST test ordered by a physician.

AST array dispenser 84 is then operated to push the lowermost AST test array 12 within second canister 18 into the second empty parallel slot 86 in AST array carrier 74. AST array dispenser 84 continues this operation in conjunction with rotation of AST canister post 20 until the number of different AST test arrays 12 as are required to perform all of the different AST tests ordered by a physician have been loaded onto AST carriers 74. Incoming patient samples are bar-coded with identifying indicia from which the AST tests that are desired to be accomplished may be established by CPU 15.

Broth is supplied to the analyzer 10 in prefilled broth containers 16 typically containing four different types of broth. CPU 15 is programmed to automatically identify the type of broth container 16 needed to perform the requested AST tests and to rotate B/ID carousel 26 to present the requisite broth container 14 to the broth container handling apparatus 108 and thereby to pipetting apparatus 46. As described previously, pipetting apparatus 46 is adapted to remove a known amount of inoculum from a sample tube 34 and deposit inoculum into broth container 14 at position 46c where inoculum and broth are mixed using a vortex mixer, and then aspirated from the broth container 14 as an inoculum-broth solution and deposited into the aforementioned inoculum-broth reservoir 134 of individual test arrays 12.

In an typical embodiment, as many as ten AST incubation racks 72 may be contained within the AST incubation and analysis chamber 70 and as many as twenty AST carriers 74 may be supported on pairs of ledges 73 in each AST incubation rack 72. The uppermost pair of ledges is reserved for used AST carriers 74 to be transferred to a disposal (not shown). An AST array reader 90 is positioned within AST incubation chamber 70 proximate the periphery of the AST incubation racks 72 and is adapted to remove a single AST array carrier 74 from any one of a plurality of pairs of AST incubation support ledges 73 (FIG. 2) or alternately support slots 77 (FIG. 2A) and to perform AST optical analysis on samples contained within the AST test arrays 12 carried by AST array carrier 74. After AST optical analysis is completed, AST array reader 90 is similarly adapted to return the AST array carrier 74 to its original position within the AST incubation rack 72. The AST reader 90 is mounted on a pair of vertically oriented shafts 92 and is movable between the next-uppermost and lowermost AST array carrier 74 within AST incubation chamber 70 so that all AST carriers 74 within AST incubation and analysis chamber 70 may be removed from all AST incubation racks 72 for testing. Each AST incubation rack 72 is attached to a rotatable platen 91 so that all AST carriers 74 may be presented as required for optical analysis to the AST reader 90.

U.S. Pat. No. 4,448,534, assigned to the assignee of the present invention, describes a scanning apparatus for performing optical density tests on liquid samples that is typical of the AST reader 90 used in analyzer 10. The apparatus of the prior patent includes an optical testing system for automatically electronically scanning each well of a multi-well test device containing several different liquid samples. Two beams of interrogating radiation from are passed through a plurality of AST test wells arrayed in two concentric circles as described later to an opposing array of photosensitive cells, one photosensitive cell for each test well. The intensity of the beam of interrogating radiation may be monitored and the associated power source adjusted using feed-back mechanisms so as to maintain a stable intensity level. There is optionally also provided a calibrating or comparison test well for receiving the radiation. Electronic apparatus read the optical signals emanating from each test well in sequence completing a scan of all test wells in the array as the test array is passed between the radiation source and the array of photosensitive cells. The resultant signals are compared with the signals from a comparison cell and with other signals or stored data, and AST determinations are made and then recorded within CPU 15 and displayed or printed out. A system of the type described above is similar to that sold under the trademarks Walk-Away® analyzer by Dade Behring Inc., Deerfield, Ill.

Figure 7:
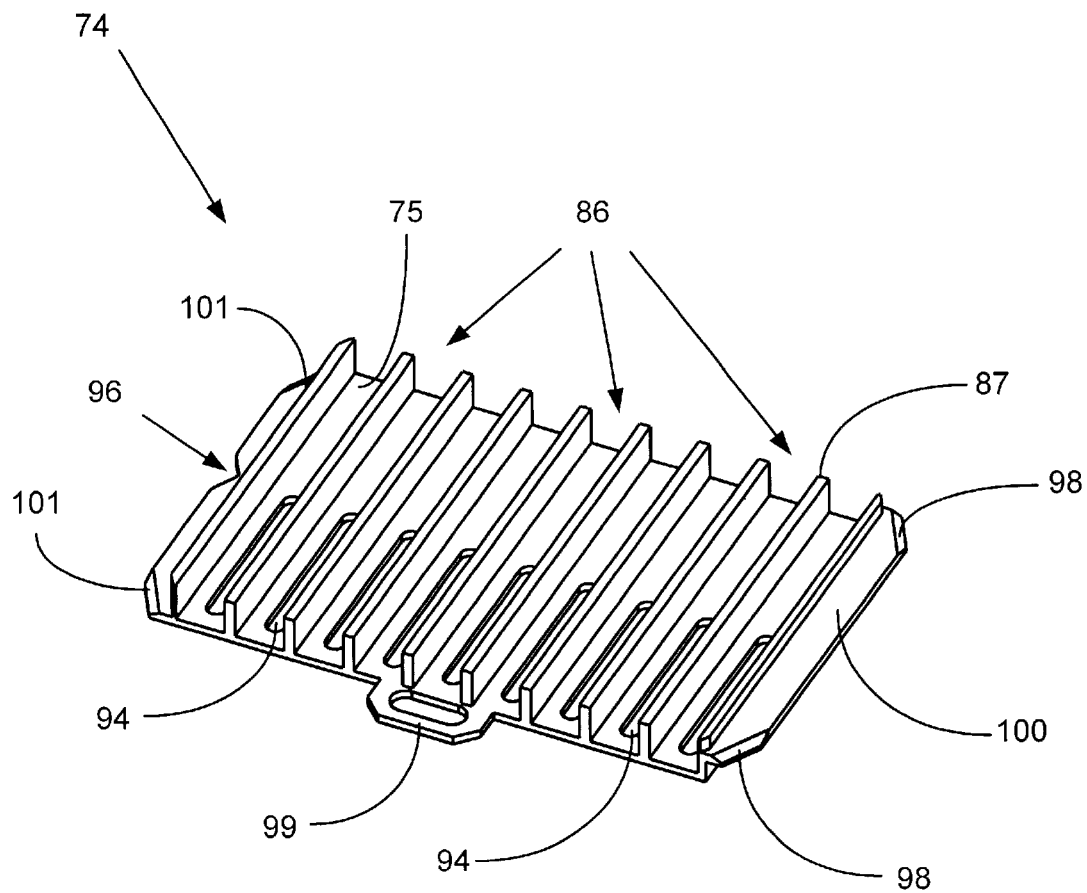
FIG. 7 is a perspective view of an AST array carrier useful within the present invention.

As seen in FIG. 7, AST array carrier 74 is formed with a number of individual parallel open slots 86, each slot 86 having an elongate optical reader opening 94 formed in the carrier base 75 of the carrier 74 to facilitate the optical measurements described above. Reader openings 94 are sized and shaped so as to allow the interrogating beam of radiation to be passed through the plurality of microwells in a AST test array 12 described hereinafter. AST array carrier 74 further includes a notch 96 and chamfered edges 101 formed in the base 75 of carrier 74 and a pair of chamfered edges 98 formed in a raised flange 100 to facilitate secure transportation of the AST array carrier 74 throughout analyzer 10. Additionally, these features, notch 96 and chamfered edges 98 and 101, are used in precisely transferring and locating a carrier 74 for optical analysis by a biasing means at notch 96 adapted to urge the carrier 74 against a stop mated with the raised flange 100. Slots 86 are defined by a number of optically opaque rails 87 extending upwardly from carrier base 75 and such rails 87 serve to maintain AST test arrays 12 in a stable and secure position within AST array carrier 74. AST array carrier 74 has a handle 99 formed in base 75 to facilitate movement of AST array carrier 74 throughout analyzer 10 as required.

Figure 2A:
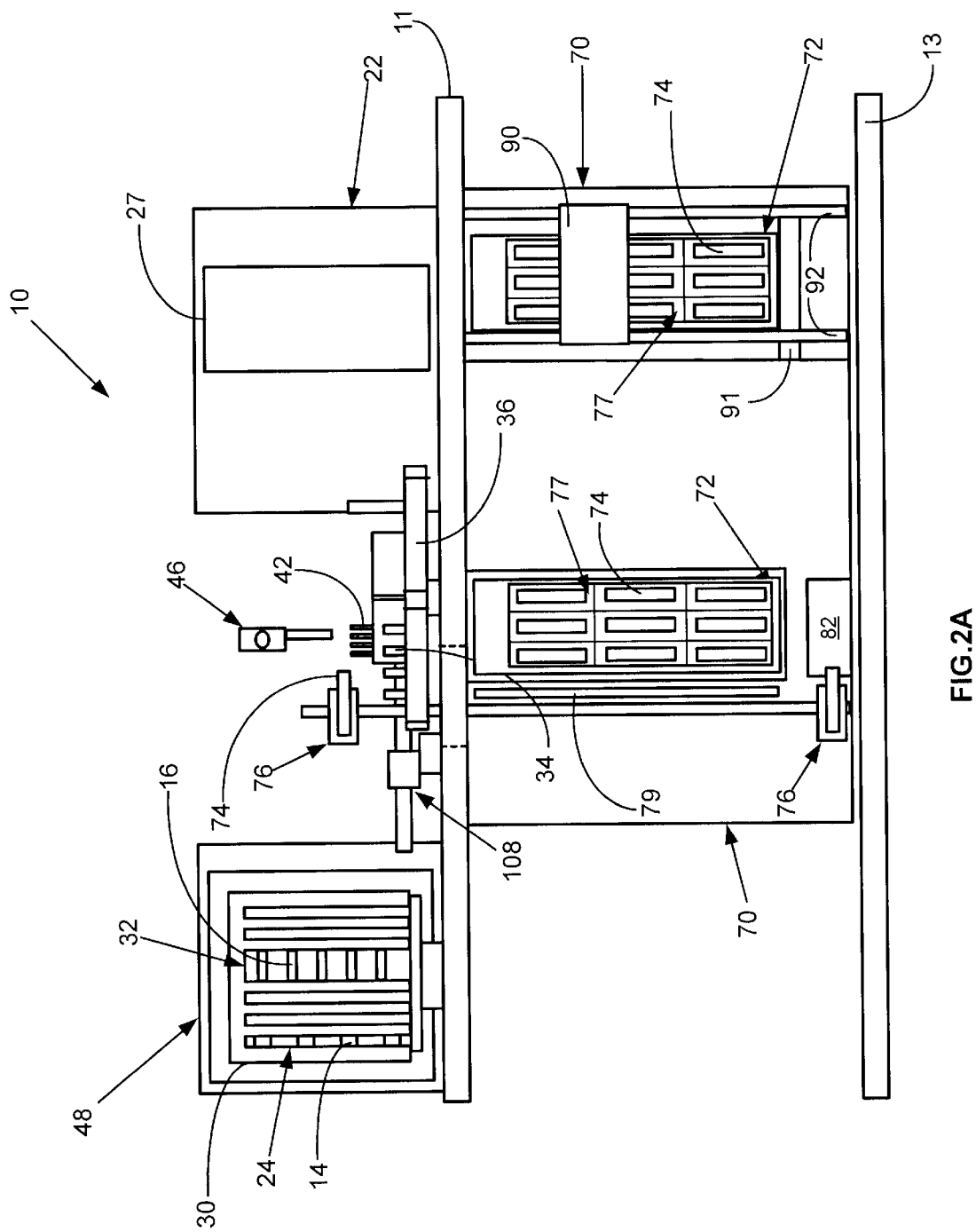
FIG. 2A is a simplified schematic elevation view of an alternate embodiment of the automated microbiological analyzer of FIG. 1.

In the embodiment of FIG. 2A, the AST carrier transporter 76 is adapted to be vertically movable from between the vacuum filling station 82 on the lower base plate 13 and the uppermost incubation support slot 77 within AST incubation and analysis chamber 70. The AST carrier transporter 76 is even further adapted to remove an AST array carrier 74 from the vacuum filling station 82, to rotate a loaded AST array carrier 74 about ninety degrees so that the central axis X—X of the AST microwells 124 carried thereby has a generally horizontal orientation and to insert the AST array carrier 74 carrying the horizontally oriented AST microwells 124 into any one of a plurality of open incubation support slots 77 inside AST incubation and analysis chamber 70. A opened second side portion 79 is formed in the exterior wall of the AST incubation and analysis chamber 70 to facilitate transfer from the AST carrier transporter 76 to the AST incubation racks 72.

Analyzer 10 comprises a multi-functional sample pipetting and delivery system 60 adapted to remove a pipette tip 42 from a pipette tip holder 40 using a pipetting apparatus 46, aspirate a known quantity of liquid sample from an open sample tube 34 held in a sample tube holder 36 and to deposit a portion of or all of the aspirated sample into either of, or both of, a broth container 14 or an ID test rotor 16. Pipetting apparatus 46 is adapted to be moved typically by a stepper motor and lead screw as controlled by CPU 15 between:

1. a first position, identified as 46a, for accessing pipette tips 42;
2. a second position, identified as 46b, for aspirating sample from sample tube 34;
3. a third position, identified as 46c, for depositing a known amount of sample into a broth container 14 and subsequently aspirating a known amount of mixed sample-broth solution from broth container 14;
4. a fourth position, identified as 46d, for depositing a known amount of mixed sample and broth into an AST test array 12;
5. and a fifth position, identified as 46e, for depositing a known amount of sample into an ID test rotor 16.

Sample pipetting and delivery system 60 moves in two opposed directions along a linear path defined by the loci L of positions 46a, 46b, 46c, 46d, and 46e. This feature of analyzer 10 simplifies movement of pipetting apparatus 46 between pipette tips 42 in pipette tip holder 40, sample tubes 34 in sample tube holder 36, broth containers 14, AST test arrays 12 within AST array carrier 74, and ID rotors 16 within filling and centrifuging apparatus 52. Positions 46a, 46b, 46c, and 46e are fixed position along loci L; however, as described in conjunction with FIG. 6, position 46d is a multiple number of locations whereat sample-broth solution is dispensed into a reservoir within AST arrays 12 to fill the arrays 12.

The sample pipetting and delivery system 60 further comprises the previously mentioned pipetting apparatus 46, broth container handling apparatus 108 adapted to remove a broth container 14 from the B/ID carousel 28 and to present the broth container 14 to the pipetting apparatus 46, and an ID rotor filling and centrifuging apparatus 52 adapted to remove an ID test rotor 16 from the ID incubation and analysis chamber 48 and to present ID test rotor 16 to the pipetting apparatus 46. ID rotor filling and centrifuge device 52 is further adapted to replace a loaded ID test rotor 16 back into the ID incubation chamber 48 after presentation to the pipetting apparatus 46. The ID rotor filling and centrifuge device 52 is even further adapted to centrifugally rotate an ID test rotor 16 after being filled with sample so as to evenly distribute sample deposited therein by the pipetting apparatus 46. Devices adapted to perform the functions of pipetting apparatus 46 are generally known and typically include stepper motor and lead screw, a vacuum operated liquid sample aspiration/disposition system, and a vertical linear drive having a tapered pipette tip mandrel at its lower extremity, the mandrel being sized for an interference fit into a pipette tip 42.

Figure 6A:
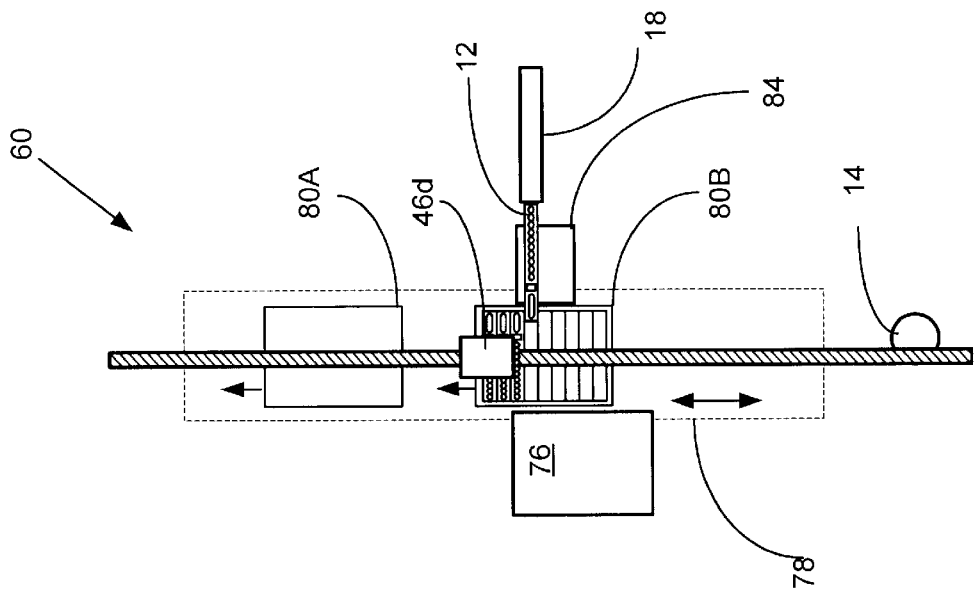
FIGS. 6A–B illustrate the functions of the sample pipetting and transport system of FIG. 3 in filling the AST test arrays of FIG. 3.
Figure 6B:
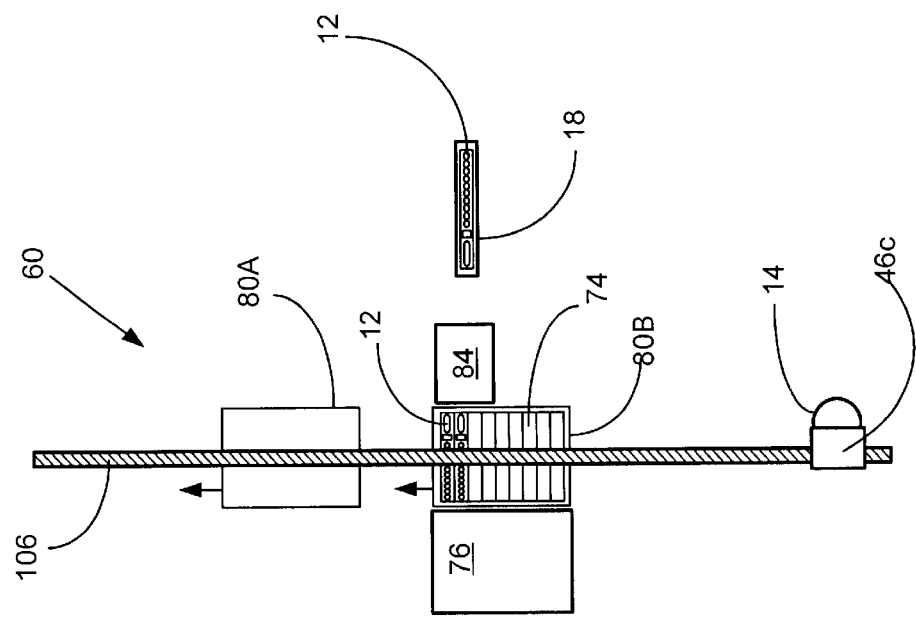

FIGS. 6A–6B are illustrative of the operation of sample pipetting and transport system 60 of FIG. 3 in filling the AST test arrays of FIG. 5 and are simplified so as to illustrate high speed filling of AST test arrays 12 and AST test microwells 124 with liquid sample aspirated from sample tubes 34 by pipetting apparatus 46. Beginning with FIG. 6A, an AST carrier 74 partially loaded with AST test arrays 12 and supported on AST array carrier bed 80B is seen positioned between AST carrier transporter 76 and AST array dispenser 84. In FIGS. 6A–6B, two identical AST array carrier beds are identified as 80A and 80B for purposes of discussion. AST array carrier bed 80A is seen as being empty in FIG. 15A. As discussed earlier, AST array dispenser 84 is adapted to remove AST test arrays 12 from an AST canister 18 in the form of a singulated stream and to successively place the AST arrays 12 within a number of empty AST array slots 86 formed within an AST carrier 74 as the AST carrier 74 is advanced along a first direction on carried by AST array carrier bed 80B (arrow pointing "upwards" in FIG. 6A for purposes of illustration) as controlled by CPU 15. As indicated by the "upwards" direction of movement arrows, hereinafter called the "upwards direction", the empty AST carrier bed 80A is seen "ahead" of AST carrier 74 on the AST array carrier bed 80B that is partially loaded with AST test arrays 12. For purposes of clarity, AST array carrier transport 78 is shown only once in dashed lines in FIG. 6B and its two directions of travel are as indicated by a double-ended arrow even though the AST array carrier transport 78 is in each of FIGS. 6A–6B.

FIG. 6B illustrates a subsequent stage of loading AST carrier 74 with AST arrays 12 whereat a fourth AST array 12 is being loaded onto AST array carrier 74; pipetting apparatus 46, having aspirated an amount of inoculum-broth solution from a broth container 14, is at position 46d and deposits a known amount of inoculum-broth solution into reservoir 134 of the first AST test array 12 loaded onto AST array carrier 74. As described before, pipetting apparatus 46 is controlled by CPU 15 between a third position, 46c, for aspirating a known amount of inoculum-broth solution from broth container 14 after the sample and broth are properly mixed together and a fourth position, 46d, for depositing a known amount of sample and broth into an AST test array 12. Pipetting apparatus 46 "chases" AST array carrier 74 "upwards" or "downwards" as required so as to deposit inoculum-broth into all AST test arrays 12 carried by AST array carrier 74, eliminating the requirement that AST arrays 12 be filled at a stationary position(s).

This process continues until the requested number of AST arrays 12 are loaded into AST array slots 86 formed within AST array carrier 74 at which stage the direction of motion of AST array carrier transport 78 reverses to a direction opposite the "upwards" direction. AST array carrier transport 78 continues in the downwards direction of movement until the empty AST array carrier bed 80A is aligned with AST carrier transporter 76 at which stage, AST array carrier transport 78 is stopped and an empty AST carrier 74 is moved by AST carrier transporter 76 onto AST array carrier bed 80A. At this stage, the direction of motion of AST array carrier transport 78 reverses once again to the "upwards direction" and the empty AST array carrier 74 is obtained by AST carrier transporter 76 from within a number of similar an empty AST carriers 74 made available within AST incubation and analysis chamber 70. During this time, pipetting apparatus 46 continues to "chase" AST array carrier 74 and deposit at the "moving" position 46d a known amount of inoculum-broth into the AST test arrays 12 on the AST array carrier 74 until all AST arrays 12 are filled. This movement in the "upwards direction" continues until the AST array carrier 74 having all filled AST arrays 12 is in alignment with AST carrier transporter 76 at which stage, not shown, AST array carrier transport 78 is stopped and AST carrier transporter 76 removes an AST array carrier 74 from AST array carrier bed 80B and lowers the AST array carrier 74 through AST transport opening 81 in operating plate 11 to a lowermost position whereat the AST carrier transporter 76 deposits the AST array carrier 74 into the AST vacuum filling station 82 positioned on the lower base plate 13. After depositing AST array carrier 74 in the AST vacuum filling station 82, AST carrier transporter 76 moves vertically along AST transport rod 83 to an AST incubation rack 72 and removes an unloaded AST carrier 76 from AST incubation and analysis chamber 70 through opened side portion 73 formed in the exterior wall of the AST incubation chamber 60.

Filling of AST arrays 12 on AST array carrier 74 by pipetting apparatus 46 continues in this process until the AST array carrier 74 contains all filled AST arrays 12 at which stage, the AST array carrier 74 is removed by AST carrier transporter 76; the direction of motion of AST array carrier transport 78 reverses once again to the "upwards direction" so that the unloaded AST array carrier 74 on 80B may next be loaded with AST arrays 12 by AST array dispenser 84. This AST array carrier 74 loading process begins and as soon as an unfilled AST array 12 is positioned upon AST array carrier 74, pipetting apparatus 46 begins depositing inoculum-broth into an AST test array 12. This situation exactly replicated the AST array loading and filling stage of FIG. 6A so that the AST array 12 filling stages depicted by FIGS. 6A–6B may be repeated as required.

During operation of analyzer 10, patient samples to be tested have bar-coded identifying indicia from which the ID and AST tests that are desired to be accomplished may be identified. Analyzer 10 is programmed using well-known computer-based programming tools to automatically perform the appropriate sample and reagent handling protocols. Computer CPU 15 thus automatically determine the numbers of different AST test arrays 12 and broth containers 14 required to complete the requested AST tests. AST canister post 20 is automatically rotated to present the AST canisters 18 containing the required AST test arrays 12 to AST array dispenser 84 and to load the AST test arrays 12 onto AST carriers 74 for transportation to various filling, incubation and testing stations.

Filled AST arrays 12, using the pipetting process described in FIGS. 6A–6B, are transported by AST carrier transporter 76 to the array filling station 82 where inoculum-broth solution is dispersed to all test microwells 124 in the individual arrays 12 using vacuum-filling means. To fill the microwells 124 with an inoculum-broth solution to be tested, pipetting system 46 dispenses a predetermined quantity of inoculum-broth solution into reservoir 134 within each AST test array 12 carried on AST carriers 74 as described in conjunction with FIG. 15. When all of the reservoirs 134 have been loaded with inoculum-broth solution, AST carrier transporter 76 moves the AST array carrier 74 to AST array vacuum filling station 82 where a clam-shell like vacuum chamber is lowered over the AST array carrier 74 and a vacuum is applied to all AST test arrays 12 carried thereon. Vacuum filling station 82 used to fill test wells in AST test arrays 12 employs techniques that are generally known in the art and typically includes means to generate and release a vacuum within an AST test array 12 and consists generally of a vacuum pump, appropriate vacuum control valves, air filters and pressure transducers that are controlled by CPU 15 to apply and release vacuum in a manner to not cause an excessive amount of bubble formation when the sealable air port 138 is sealed and the AST test array 12 released to atmospheric pressure. When vacuum is applied around the test arrays 12, air is removed from all AST microwells 124 through the sealable vacuum port 138 which is in fluid communication with individual AST microwells 124 by means of microchannels 142 and 143. Subsequent to this evacuation process, a source of heat may be brought in contact with vacuum port 138 for a predetermined time to seal or close port 138 against air flow when vacuum is released; once port 138 is sealed, the vacuum is released within vacuum chamber. Alternately, a resilient stopper may be pressed against an air port separate from the evaporation well. Atmospheric pressure over the inoculum-broth solution in reservoir 134 causes inoculum-broth solution to flow through opening 140 into microchannels 130, 142 and 143 thereby filling the sacrificial evaporation well 132 and into all microwells 124 in each of the AST test arrays 12 carried by AST array carrier 74. As the microwells 124 are filled with inoculum-broth solution, air trapped within the chamber 158 is intended to flow into the small recessed top edge portion 160 which acts as a bubble trap within microwell 124.

The AST test arrays 12 are removed from vacuum filling station 82 and transported to the analysis and incubation chamber 70 by AST carrier transporter 76. AST testing may be accomplished within analysis and incubation chamber 70 by AST array reader 90 using a beam of interrogating radiation from above or below each AST array 12 through the polished central arc portion 157 of the top surface 150 of each microwell 124 and measuring the degree of absorption or change in color or generation of a fluorescent signal using a calorimetric or fluorometric photodetector located below or above each microwell 124. In a first embodiment of the present invention, prior to AST testing, in order to ensure that unwanted air bubbles will not interfere with optical measurements performed on liquids contained in microwells 124, a process like that illustrated in FIGS. 9A–9G may be conducted. FIG. 9A shows air pockets or bubbles 160A not captured within bubble trap 160 during the vacuum filling process of FIGS. 8A–8D.

Figure 9D:
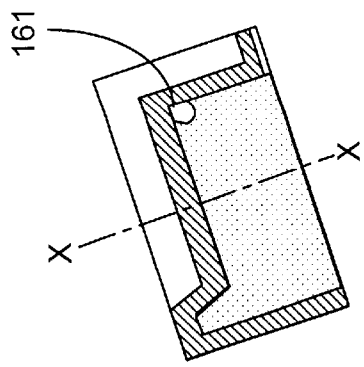
FIGS. 9A–G are illustrative of one method to trap air within the AST test array of FIG. 3; and, FIGS. 10A–C are illustrative of an optical interrogation process of the present invention using the AST test array of FIG. 5A.
Figure 9C:
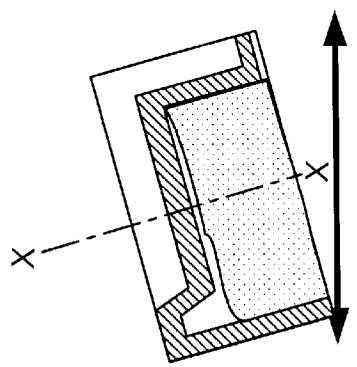
Figure 9B:
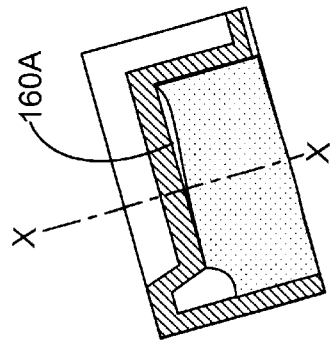
Figure 9A:
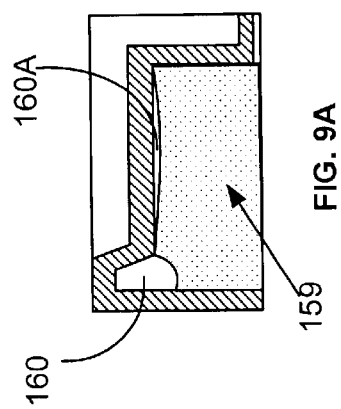
Figure 9G:
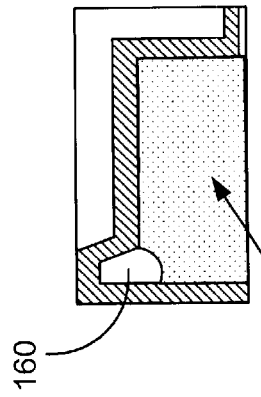
Figure 9F:
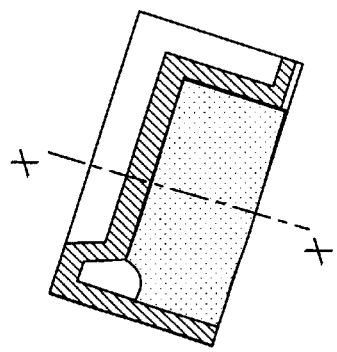
Figure 9E:
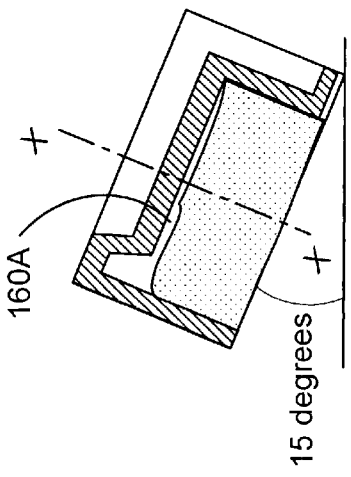

It has been discovered that such unwanted air bubbles 160A may be eliminated by tilting AST arrays 12 in a first direction, FIG. 9B, to move air trapped in a bubble trap 160 out from the trap 160 and air bubbles 160A located along the upper surface of the microwell 124 and then agitated, for instance by back-and-forth motion in an horizontal plane, indicated by the double-ended arrow in FIG. 9C, so that all air is caused to move to an upper microwell corner 161 opposed to the location of trap 160, FIG. 9D. The array is then tilted in the direction opposite to that of FIG. 9C, as shown in FIG. 9E, so that all air is caused to be swept along the upper inner surface of microwell 124, thereby to capture all air bubbles 160A within microwell 124 into bubble trap 160, FIG. 9F. Prior to testing, the array 12 is returned to its original position, FIG. 9G. In this embodiment, during testing and after the process of FIGS. 9A–9G, the AST arrays 12 are oriented such that the microwell axis X—X is generally vertically directed and the beam of interrogating radiation passes along the axis X—X from above or beneath microwell 124 of FIG. 5 in the analyzer of FIG. 2.

In an alternate embodiment of the present invention, depicted in FIG. 10A–C, after AST test arrays 12 are removed from vacuum filling station 82 and transported to the analysis and incubation chamber 70, the AST test arrays 12 are re-oriented by ninety degrees so that the microwell axis X—X is generally horizontally directed. (The arrow pointing upwards in FIGS. 10A and 10C is in the vertical direction, defined by the direction of gravitational forces.) FIG. 2A illustrates AST incubation and analysis chamber 70 having rotatable AST incubation racks 72 adapted to support a number of vertically oriented AST carriers 74 in open support slots 77, thereby to hold a number of AST test arrays 12 in the re-oriented position so that each microwell 124 therein has a horizontally directed microwell axis X—X, as seen in FIG. 10C. At predetermined time intervals during the incubation process, AST carriers 74 are moved by robotic means ( not shown) into AST array reader 90 in this re-oriented position, as schematically depicted in FIG. 1A. FIG. 10B shows a top plan view of the AST array 12 of FIG. 10A, and also schematically depicts a conventional radiation source 170 and radiation detection photocell 172 adapted to generate and capture, respectively, a beam of interrogating radiation along axis X—X of each microwell 124 in the AST arrays 12 supported within AST carriers 74. FIG. 10C is an enlarged schematic view of a single microwell 124 illustrating the interrogating radiation 168 passing along the axis X—X of generally horizontally orientated AST microwells 124 and captured by radiation photocell 172. During AST reading, the left-most microwells 124 in AST arrays 12 are read simultaneously; the radiation source 170 and radiation detection photocell 172 are then moved step-wise left-to-right (indicated by dashed arrows in FIG. 10B) along the array of microwells 124, stopping at each successive microwell to make AST test readings. In this manner, crosstalk signals from next adjacent microwells 124 in a single array 12 are minimized. As previously described, next adjacent AST arrays 12 are separated from one another by optically opaque rails 87 extending upwardly from carrier base 75 of AST carriers 74 so as to also minimize crosstalk signals from next adjacent AST arrays 12.

Figure 5A:
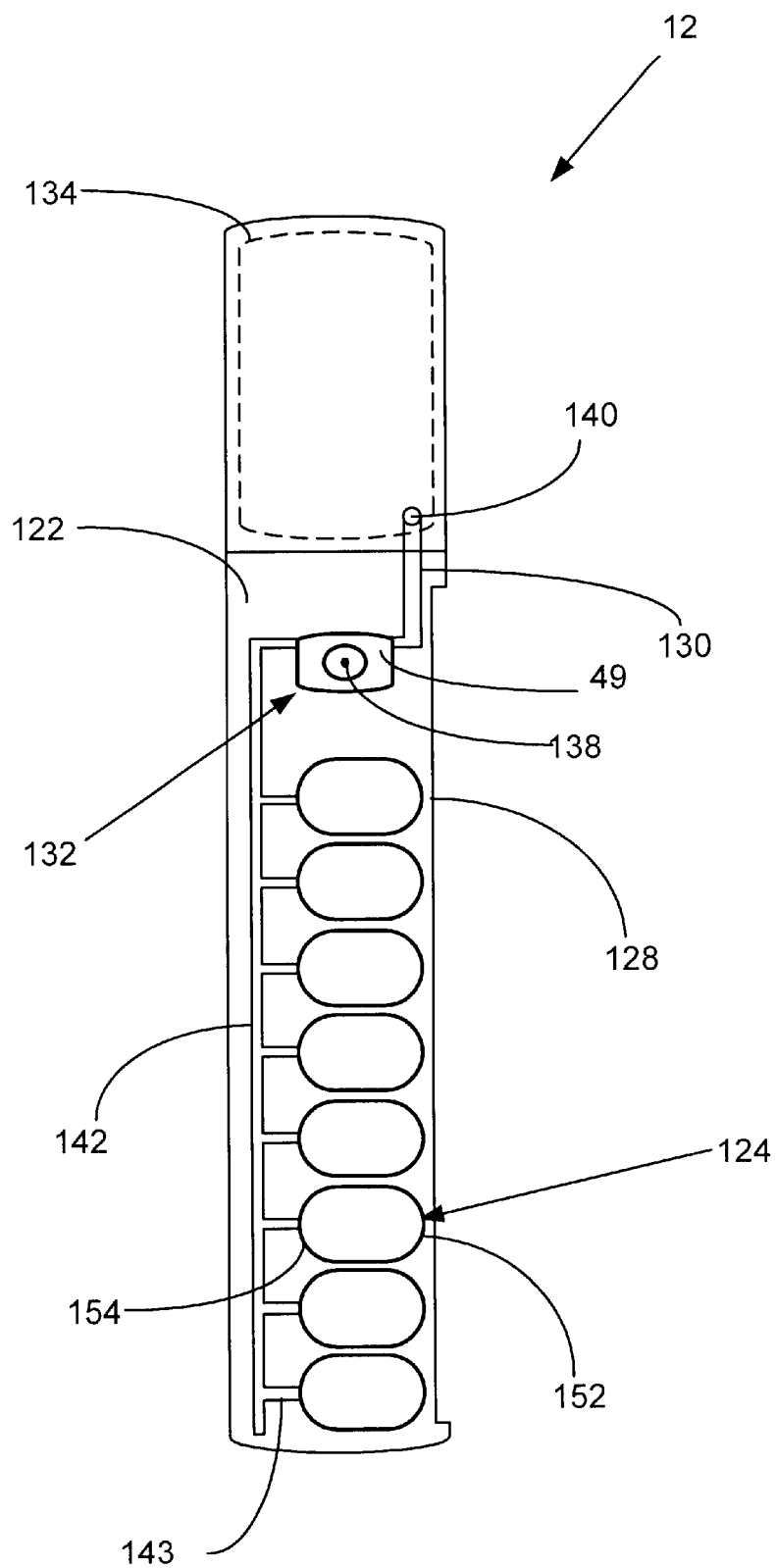
FIG. 5A is a bottom view of an alternate embodiment of an AST test array useful within the analyzer of FIG. 2A.

In this preferred embodiment of the present invention, due to the horizontal orientation of the AST microwells 124, gravitational forces acting on the liquid solution within microwells 124 are greater than gravitational forces acting on any gaseous air trapped within test solution 159 contained in microwell 124. Consequently, test solution is pulled downwards by gravity and away from the uppermost sidewall 156 forcing the lighter gaseous air bubbles remaining in the microwells 124 to move upwards to the uppermost sidewall 156 and out of the path of optical measurements performed on liquid solutions contained in microwells 124. It should be noted as illustrated in FIG. 10C that bubble trap 160 is no longer used in microwell 124 to trap air into a single pocket. Prior to testing, AST carriers 74 are vibrated slightly by a piezoelectric device 91 or caused to orbit around the X—X axis of microwells 124 by a mechanical wheel 93 within reader 90 to re-suspend or mix the solution contained within the microwells 124. In this preferred embodiment, the interior of each AST test microwell is formed with the shape of a smooth elongate oval and does not include a separate bubble trap as shown in FIG. 5A. During the time AST carriers 74 are caused to orbit around the X—X axis of microwells 124, prior to AST testing, air within microwell 124 sweeps along the interior surface of the microwells 124 and aids in agitation and re-suspension of the solution within AST reaction chamber 158.

It is to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

What is claimed is:

1. An method to perform antibiotic testing of a test solution contained within microwells of a test array, the test array formed as an elongate shaped body with opposed and parallel top and bottom surfaces, said body containing a plurality of upwardly projecting test microwells formed in the bottom surface, each microwell having a central axis projecting upwardly from the bottom surface of the array through the top surface of the microwell, the test method comprising:

orienting the central axis of each microwell in a generally horizontal direction during antibiotic testing so that air within the interior of the microwell moves away from the center axis; and, directing a beam of interrogating radiation along the central axis.

2. The method of claim 1 wherein the test array is formed without including a bubble trap.

3. The method of claim 1 wherein the interior of each test microwell has the shape of a smooth elongate oval without including a bubble trap.

4. The method of claim 1 wherein in a step prior to performing antibiotic testing of a test solution contained within the microwells, the microwells are caused to orbit around their central axis so as to re-suspend or mix the solution contained within the microwells.

5. The method of claim 1 wherein antibiotic testing comprises moving a radiation source and radiation detector step-wise along the array of microwells in a plurality of test arrays and stopping at each successive microwell to make test readings, so that crosstalk signals from next adjacent microwells are minimized.

6. A method to perform antibiotic testing of a test solution contained within microwells of a test array, the test array formed as an elongate shaped body with opposed and parallel top and bottom surfaces, said body containing a plurality of upwardly projecting test microwells formed in the bottom surface, each microwell having an integral bubble trap and a central axis projecting upwardly from the bottom surface of the array through the top surface of the microwell, the test method comprising:

tilting the test array in a first direction to aid in removing air trapped in the bubble trap;

agitating the test array so that air located within the bubble trap and along the inner top surface of each microwell is caused to move to an upper microwell corner opposed to the location of the bubble trap;

tilting the test array in the direction opposite to the first direction, so that air is caused to be swept along the inner top surface of each microwell, thereby to capture all air bubbles within the microwell into the bubble trap; and, returning the array to a position such that the central microwell axis is generally vertically directed.

7. The method of claim 6 wherein antibiotic testing comprises directing a beam of interrogating radiation along the vertically oriented central axis.

8. The method of claim 7 wherein antibiotic testing comprises moving a radiation source and radiation detector step-wise along the array of microwells in a plurality of test arrays and stopping at each successive microwell to make test readings, so that crosstalk signals are minimized.

* * * * *